(12) United States Patent
Larson et al.

(10) Patent No.: US 8,262,633 B2
(45) Date of Patent: Sep. 11, 2012

(54) ABSORBENT ARTICLE HAVING A MULTI-COMPONENT VISUAL SIGNAL

(75) Inventors: Signe Christina Larson, Cincinnati, OH (US); Lisa June Hood, Cincinnati, OH (US); David Christopher Oetjen, West Chester, OH (US); John Lee Hammons, Hamilton, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 441 days.

(21) Appl. No.: 12/548,603

(22) Filed: Aug. 27, 2009

(65) Prior Publication Data

US 2010/0036351 A1 Feb. 11, 2010

Related U.S. Application Data

(63) Continuation-in-part of application No. 12/188,543, filed on Aug. 8, 2008, now Pat. No. 7,967,801, and a continuation-in-part of application No. 12/188,598, filed on Aug. 8, 2008, now Pat. No. 8,058,501.

(51) Int. Cl.
*A61F 13/15* (2006.01)
*A61F 13/20* (2006.01)

(52) U.S. Cl. .............. 604/385.01; 604/385.101; 604/378

(58) Field of Classification Search ............. 604/385.01, 604/378, 385.101
See application file for complete search history.

(56) References Cited

U.S. PATENT DOCUMENTS

| | | | |
|---|---|---|---|
| 4,673,403 A | 6/1987 | Lassen et al. | |
| 5,647,863 A * | 7/1997 | Hammons et al. | 604/378 |
| 7,322,472 B2 * | 1/2008 | Swiecicki et al. | 206/459.1 |
| 7,718,844 B2 * | 5/2010 | Olson | 604/361 |
| 7,736,688 B2 * | 6/2010 | Oetjen et al. | 427/2.1 |
| 2003/0078553 A1 | 4/2003 | Wada et al. | |
| 2004/0131820 A1 * | 7/2004 | Turner et al. | 428/92 |
| 2004/0170813 A1 * | 9/2004 | Digiacomantonio et al. | 428/195.1 |
| 2005/0154365 A1 * | 7/2005 | Zander et al. | 604/385.04 |
| 2006/0025735 A1 * | 2/2006 | Berg et al. | 604/385.01 |
| 2006/0025736 A1 * | 2/2006 | Berg et al. | 604/385.01 |
| 2007/0087169 A1 * | 4/2007 | McFall | 428/172 |
| 2007/0293834 A1 * | 12/2007 | Miura et al. | 604/385.01 |
| 2009/0281513 A1 * | 11/2009 | Nelson | 604/379 |
| 2010/0036351 A1 * | 2/2010 | Larson et al. | 604/385.01 |

OTHER PUBLICATIONS

PCT International Search Report dated Jun. 14, 2010.

* cited by examiner

*Primary Examiner* — Tatyana Zalukaeva
*Assistant Examiner* — Ginger T Chapman
(74) *Attorney, Agent, or Firm* — Megan C. Hymore; Andrew J. Hagerty; Gary J. Foose (57) ABSTRACT

An absorbent article having a central colored region, an intermediate colored region, an outer colored region, and a background region. The intermediate colored region can be between the central colored region and the outer colored region. The intermediate colored region can substantially circumscribe the central colored region. The central colored region, intermediate colored region, and outer colored region differ in color from the background region.

20 Claims, 5 Drawing Sheets

ABSORBENT ARTICLE HAVING A MULTI-COMPONENT VISUAL SIGNAL

CROSS REFERENCE TO RELATED APPLICATION

This application is a continuation-in-part of application Ser. No. 12/188,543, filed Aug. 8, 2008 now U.S. Pat. No. 7,967,801. This application is a continuation-in-part of application Ser. No. 12/188,598, filed Aug. 8, 2008 now Pat. No. 8,058,501.

FIELD OF THE INVENTION

The invention provides an absorbent article having a multi-component visual signal.

BACKGROUND OF THE INVENTION

A variety of absorbent articles that include different colored regions are available in the market. Absorbent articles such as sanitary napkins and female adult incontinence articles that function to collect fluid discharged from a woman's vagina or urethra sometimes include a colored region proximal the central portion of the absorbent article that differs in color from portions of the absorbent article remote from the central portion of the absorbent article.

By including a colored region in the central portion of the absorbent article, manufacturers of absorbent articles have effectively taught consumers that the central portion of the absorbent article is where the fluid collected should reside. Manufacturers have devised a variety of designs for central colored regions. In some absorbent articles, the central colored region is relatively narrow as compared to the overall width of the absorbent article and extends only along about one-half of the length of the absorbent article. One possible reason that relatively narrow central colored regions were adopted was that such colored regions could provide a desired visual impression, such as the impression of depth. Central colored regions also might help the consumer understand how her use and placement of the product in her panty might be affecting the staining pattern of absorbent article, which might help her improve how and where she mounts the chassis of the absorbent article in her panty to achieve maximum performance.

One problem associated with narrow central colored regions on absorbent articles is that some consumers associate stain patterns that extend outside the central colored region as indicating that the absorbent capacity of the absorbent article is exhausted. In some absorbent articles, the central colored region could account for less than 25% of the absorbent capacity of the absorbent article.

A variety of materials having outstanding widthwise and lengthwise fluid distribution properties are available. Such materials can distribute collected fluid to regions of the absorbent article remote from the central colored region. An absorbent article capable of more widely distributing fluid in the absorbent article can be advantageous because wider fluid distribution can effectively increase the absorbent capacity of the absorbent article. One drawback to widely distributing fluid in an absorbent article is that the stains of such fluid might travel well beyond the central colored region, if present. As mentioned above, stains outside of the central colored region might be alarming to the wearer. Making the central colored region larger may not be an attractive design option because larger colored regions might make the absorbent article appear to be bulkier and be perceived as not providing for comfortable fit.

With these limitations in mind, there is a continuing unaddressed need for absorbent articles having a visual impression that that are perceived by wearers as having adequate fluid storage capacity to meet their needs. Further, there is a continuing unaddressed need for absorbent articles that reassure the user that fluid in the absorbent article in regions outside of a relatively narrow colored region is securely retained in the absorbent article and she need not worry about a leak.

SUMMARY OF THE INVENTION

Disclosed is an absorbent article having a centroid, a longitudinal centerline, a transverse centerline orthogonal to the longitudinal centerline and intersecting the longitudinal centerline at the centroid, and a body facing surface. The absorbent article comprises a background region. The absorbent article comprises a central colored region coincident with the longitudinal centerline. The absorbent article comprises an intermediate colored region substantially circumscribing the central colored region, wherein a portion of the intermediate colored region extends across the longitudinal centerline, wherein along the transverse centerline part of the background region is between the intermediate colored region and the central colored region. The absorbent article comprises an outer colored region, wherein at least part of the background region is between the outer colored region and the intermediate colored region. The background region, the central colored region, the intermediate colored region, and the outer colored region are viewable from the body facing surface. The central colored region, the intermediate colored region, and the outer colored region differ in color from the background region.

DETAILED DESCRIPTION OF THE INVENTION

"Absorbent articles" as referred to herein can be sanitary napkins, pantiliners, or incontinence pads that are worn in the crotch region of an undergarment. It is conceivable that baby diapers, adult incontinence diapers, and human waste management devices might benefit from the present invention even though they are conventionally not worn in conjunction with an undergarment. Absorbent articles can be disposable absorbent articles.

The term 'color' as referred to herein includes any primary color, i.e., white, black, red, blue, violet, orange, yellow, green, and indigo as well as any declination thereof or mixture thereof. The term 'non-color' or 'non-colored' refers to the color white which is further defined as those colors having an $L^*$ value of at least 80, an $a^*$ value equal to $0\pm2$, and a $b^*$ value equal to $0\pm2$.

The term 'disposable' is used herein to describe absorbent articles that are not intended to be re-launched or otherwise restored or reused as absorbent articles (i.e., they are intended to be disposed of after a single use).

Non-limiting examples of panty liners and sanitary napkins which may be provided with multi-component visual signal include those manufactured by The Procter & Gamble Company of Cincinnati, Ohio, such as ALWAYS ULTRA, ALWAYS INFINITY, and ALWAYS pantiliners. Absorbent articles such as those disclosed in U.S. Pat. Nos. 4,324,246, 4,463,045, 6,004,893, 4,342,314, 4,463,045, 4,556,146, 4,589,876, 4,687,478, 4,950,264, 5,009,653, 5,267,992, and Re. 32,649 are also contemplated as being absorbent articles that might benefit from such a multi-component visual signal.

Figure 1:
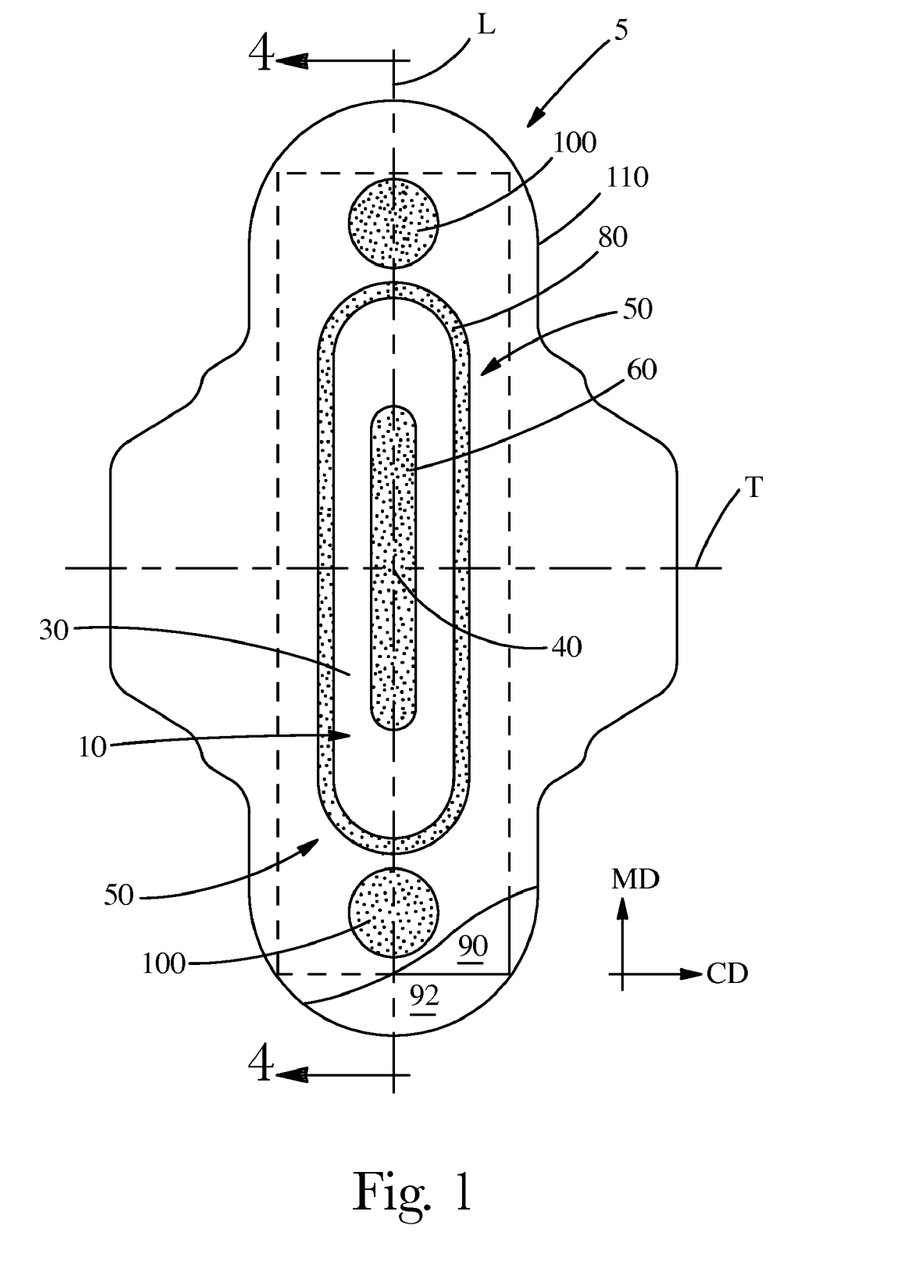
FIG. 1 is a schematic of an absorbent article.

A top view of an absorbent article 5 is shown in FIG. 1. The absorbent article 5 can have a substantially planar configuration and a centroid 40. The centroid 40 can be the intersection between the longitudinal centerline L and transverse centerline T. The absorbent article 5 can have a body facing surface 10 and a garment facing surface. The absorbent article 5 can have a machine direction MD and a cross machine direction CD, these terms being used as they are commonly used by those having ordinary skill in the art.

As shown in FIG. 1, the absorbent article 5, can be considered to have a viewing surface that is the body facing surface 10. The body facing surface 10 can be the side of the absorbent article 5 that is in contact the wearer's body when the absorbent article 5 is worn, as might be the case for a sanitary napkin, panti-liner, or adult incontinence product, or is inserted into the wearer's body, as might be the case for a tampon. For a generally cylindrical tampon, the longitudinal centerline L is considered to be on the body facing surface 10 of the tampon, aligned with the central axis of the tampon and the centroid 40 can be the midpoint of the longitudinal centerline L. The absorbent article 5 can have a central colored region 60, an intermediate colored region 80, and an outer colored region 100. The central colored region 60, intermediate colored region 80, and outer colored region 100 can be viewable from the body facing surface 10.

When the body facing surface 10 of the absorbent article 5 is viewed, the absorbent article 5 can have a background region 50. The background region 50 is a region that is visually distinguishable from the central colored region 60, the intermediate colored region 80, and the outer colored region 100. The background region 50 can be white or any other color visually distinguishable from the central colored region 60, the intermediate colored region 80, and the outer colored region 100. Two colors are believed to be visually distinguishable if there is a ΔE, which is discussed further below, between the two colors of at least about 1. Two colors can be more visually distinguishable if there is a ΔE between the two colors of at least about 3.

The central colored region 60 can be coincident with the longitudinal centerline L. The central colored region 60 can be part of the topsheet 30. The central colored region 60 can be part of the absorbent core 90, the absorbent core 90 being disposed between the topsheet 30 and the backsheet 92. The central colored region 60 can be positioned on a layer intermediate the topsheet 30 and the absorbent core 90. The central colored region 60 need only to be visually perceptible when the body facing surface 10 is presented to the viewer. The central colored region 60 can be provided by printing, pigmenting, dyeing, or other known means for creating a contrast in color of a substrate. Providing the central colored region 60 coincident with the longitudinal centerline L can make the absorbent article 5 to appear to be thicker than an absorbent article 5 that is devoid of a central colored region 60. The central colored region 60 can be coincident with the centroid 40, which might make the absorbent article appear to be more symmetric, which might be perceived as providing for better fit and performance. The entire outer colored region 100 can be positioned away from the transverse centerline T such that no part of the outer colored region 100 intersects the transverse centerline T.

The central colored region 60, as shown in FIG. 1, can be a substantially elongated shape. Without being bound by theory, it is believed that elongated shapes that are aligned with or on the longitudinal centerline L may make the absorbent article 5 look as if the absorbent article 5 is slim as compared to an absorbent article 5 devoid of such an elongated shape. A consumer might associate such an impression with a belief that the apparently narrow absorbent article will fit comfortably in the crotch of her panty. The central colored region 60 can have a width less than about 50% of the maximum distance between portions of the periphery 110 coincident with the transverse centerline T.

The intermediate colored region 80 can substantially circumscribe the central colored region 60. By substantially circumscribe, it is meant that more than π radians around the center of mass of the central colored region 60 is circumscribed by the intermediate colored region 80, which corresponds to the intermediate colored region 80 radially circumscribing more than about 50% of the central colored region 60. More than about 1.5π radians around the center of mass of the central colored region 60 can be circumscribed by the intermediate colored region 80, which corresponds to the intermediate colored region 80 radially circumscribing more than about 75% of the central colored region 60. More than about 1.8π radians around the center of mass of the central colored region 60 can be circumscribed by the intermediate colored region 80, which corresponds to the intermediate colored region 80 radially circumscribing more than about 90% of the central colored region 60. Without being bound by theory, it is believed that the intermediate colored region 80 might be understood by wearers as an intermediate portion of the absorbent article 5 beyond which if staining occurs, the wearer should consider being more alert to the potential need to change the absorbent article 5 in the proximal future. The intermediate colored region 80 can be provided by printing, pigmenting, dyeing, or any other known means for creating a contrast in color of a substrate.

An outer colored region 100 can be positioned such that the intermediate colored region 80 is positioned between the central colored region 60 and the outer colored region 100. Providing an outer colored region 100 such that the intermediate colored region 80 is between the outer colored region 100 and the central colored region 60 is thought to possibly provide several benefits. For instance, for absorbent articles 5 capable of laterally distributing collected fluid, stains in the absorbent article 5 that appear beyond the intermediate colored region 80 need not worry the wearer because the absorbent article 5 likely has sufficient absorbent capacity to contain additional fluid. By providing an outer colored region 100 outwards of the central colored region 60 and intermediate colored region 80, the wearer of the absorbent article 5 might better understand that the portion of the absorbent article 5 comprising the outer colored region 100 has additional fluid storage capacity because the wearer might understand that the outer colored region 100 is placed in such location to indicate to the wearer that staining in that location is not necessarily undesirable. The outer colored region 100 can be provided by printing, pigmenting, dyeing, or other known means for creating a contrast in color of a substrate.

The central colored region 60 and intermediate colored region 80 can be spaced apart from one another. Such an arrangement can be desirable so that poor registration of the central colored region 60 and the intermediate colored region 80 that might occur during manufacturing might be obscured as compared to a design in which the central colored region 60 and intermediate colored region 80 are butted up against one another. Alternatively, the intermediate colored region 80 can be positioned substantially adjacent to the central colored region 60. Such an arrangement might be useful in that staining that occurs in an intermediate colored region 80 that is substantially adjacent the central colored region 60 can provide an indication to the wearer that increased vigilance by the wearer might be advisable as the generally central portion of the absorbent article may be approaching capacity.

The outer colored region 100 can be positioned on the longitudinal centerline L. Without being bound by theory, an outer colored region 100 positioned on the longitudinal centerline L is thought to provide the benefit that when staining occurs in such an area, that the wearer should be prepared to change the absorbent article within a relatively short period of time.

In some embodiments, at least part of the background region 50 can be between the outer colored region 100 and the intermediate colored region 80. Such an approach is thought to provide for a background region 50 and outer colored region 100 that are perceptibly distinct from one another. Similarly, along the transverse centerline T, part of the background region 50 can be between the intermediate colored region 80 and the central colored region 60, to provide for perceptibly distinct regions.

The absorbent article 5 can comprise two outer colored regions 100 disposed such that the two outer colored regions 100 are positioned on the longitudinal centerline L and the central colored region 60 is between the two outer colored regions 100. Such an arrangement might be desirable in that the two outer colored regions 100 will tend to be located towards the front (oriented towards the pubic region) and back ends (oriented towards the anal region) of the absorbent article and staining in the outer colored regions 100 can be an indicator that the absorbent article 5 should be changed. Arranged as such, the intermediate colored region 80 can be between each outer colored region 100 and the central colored region 60.

The central colored region 60 can have a central colored region area that is between about 15% and about 50% of the area of the absorbent core 90 measured in the MD-CD plane. The outer colored region can be less than about 15% of the area of the absorbent core 90 in the MD-CD plane.

Figure 2:
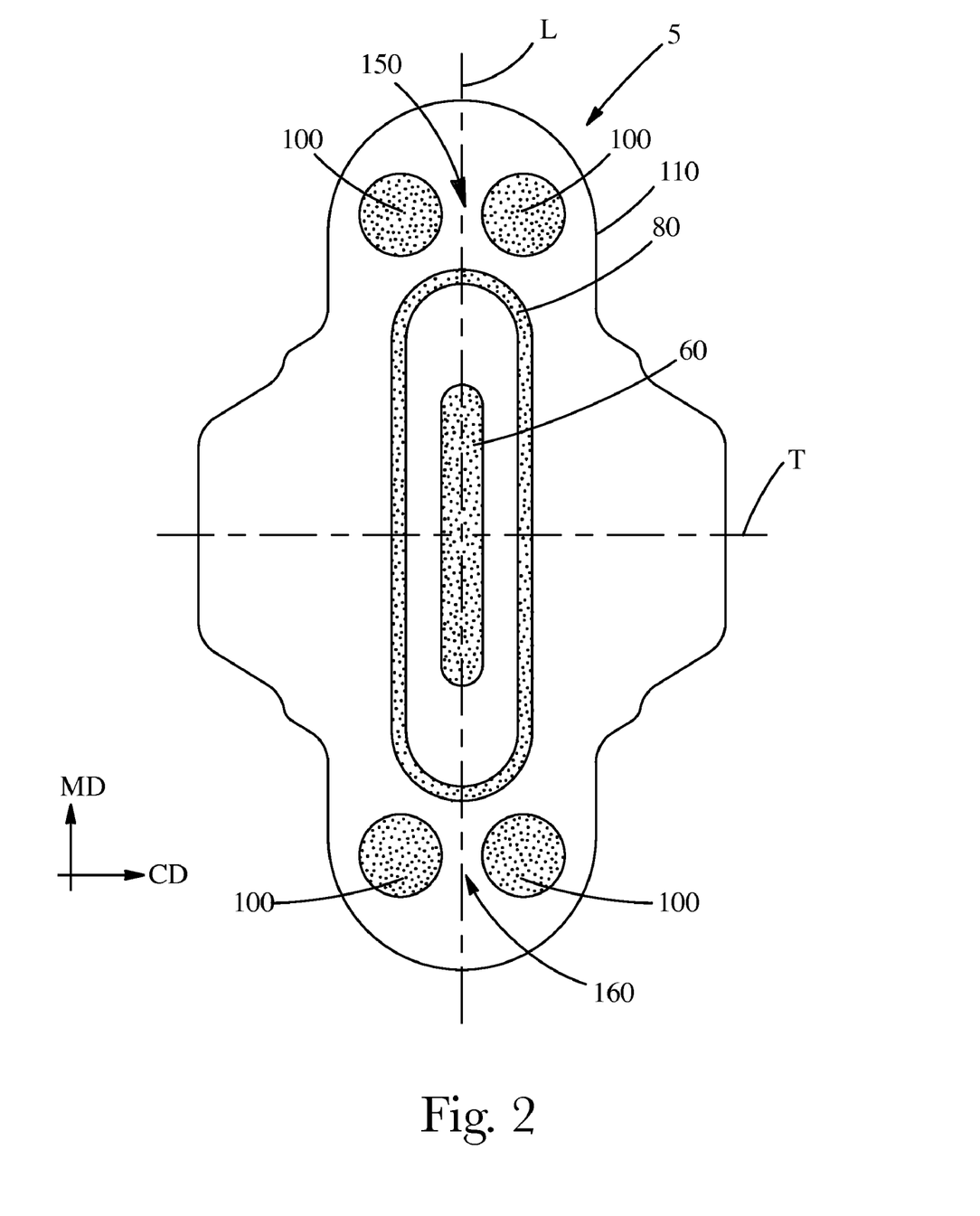
FIG. 2 is a schematic of an absorbent article.

As shown in FIG. 2, the absorbent article 5 can comprise two outer colored regions 100 in which the two outer colored regions 100 are spaced apart from one another such that the longitudinal centerline L is between the two outer colored regions 100. By placing two outer colored regions 100 on opposing sides of the longitudinal centerline L, the outer colored regions 100 are located somewhat in proximity to the periphery 110 of the absorbent article 5. As such, staining occurring in the outer colored regions 100 located in proximity to the periphery 110 can be an indicator that the absorbent article 5 is approaching or has absorbed the maximum amount of fluid that the absorbent article 5 is designed to store. In another embodiment, the absorbent article 5 can comprise two outer colored regions 100 that are spaced apart from one another such the transverse centerline L is between the two outer colored regions 100.

The absorbent article 5 can be considered to have a first end 150 and a second end 160. The first end 150 and second end 160 can be considered to be on opposing sides of the transverse centerline T. The first end 150 can comprise two outer colored regions 100 on opposing sides of the longitudinal centerline L. Similarly, the second end 160 can comprise two outer colored regions 100 on opposing sides of the longitudinal centerline. Structured as such, the absorbent article can comprise four outer colored regions 100 dispersed away from the central colored region 60. As the absorbent article 5 might have the capacity to absorb fluid in these outer colored regions 100 remote from the most central portion of the absorbent article 5, the outer colored regions 100 can indicate to the wearer that the staining in such areas is not a cause for immediate alarm. The first end 150 can be the end of the absorbent article 5 oriented towards the wearer's pubic area when worn and the second end 160 can be the end of the absorbent article 5 oriented towards the wearer's anal area when worn.

In some embodiments, it may be desirable to have the background region 50 completely frame at least the central colored region 60. For instance, the background region 50 can be between the central colored region 60 and the periphery 110, as shown in FIGS. 1 and 2. In effect, the central colored region 60 is set off or distinct from the periphery 110 so that the central colored region 60 does not contact the periphery 110. This may be desirable because for many absorbent articles 5 in which the periphery 110 comprises a bond between the topsheet 30 and backsheet 92, the bond might not be absorbent and a central colored region 60 in contact with such bond might be misunderstood by the wearer as being absorbent. For the same reason as above, the central colored region 60, intermediate colored region 80, and outer colored region 100 or outer colored regions 100 might be substantially surrounded by the background region 50. That is, the background region 50 could be between the periphery 110 and the any of the central colored region 60, intermediate colored region 80, and outer colored region 100 or outer colored regions 100.

To provide for more visually coherent designs, the central colored region 60, the intermediate colored region 80, and outer colored region 100 can be within a CIELab color space volume of less than about 200. CIELab color space volume is discussed in more detail below. With such an approach, the colors of the central colored region 60, intermediate colored region 80, and outer colored region 100 do not differ substantially to the eye of most viewers and viewers might perceive the colors to be shades or subtle variations of the same color. Subtle variations in color are thought to be pleasing to the eye, much like sample paint chips having slightly varying colors that can be pleasurable and interesting to view. If less distinctiveness between the central colored region 60, intermediate colored region 80, and outer colored region 100 is desired, the central colored region 60, intermediate colored region 80, and outer colored region 100 can be within a CIELab color space volume of less than about 50.

When the body facing surface 10 of the absorbent article 5 is viewed, the background region 50, central colored region 60, intermediate colored region 80, and outer colored region 100 are viewable by an observer. The central colored region 60, intermediate colored region 80, and outer colored region 100 are visibly distinct from the background region 50 in that central colored region 60, intermediate colored region 80, and outer colored region 100 each differ in color from the background region 50. The central colored region 60 and the background region 50 can differ in color by a ΔE, which is discussed in more detail below, of at least about 1. Similarly, the intermediate colored region 80 and the background region 50 can differ in color by a ΔE of at least about 1 so that the intermediate colored region 80 is noticeable against the background region 50. The outer colored region 100 and the background region 50 can differ in color by a ΔE of at least about 1. To provide for simple manufacturing, the central colored region 60, intermediate colored region 80, and outer colored region 100 can be provided on a first layer of material in the absorbent article 5.

The central colored region 60 can be darker than the outer colored region 100. The darkness of a color can be quantified as L, discussed below, with lower values of L corresponding to darker colors. Such a design might be useful for situations in which the central portion of the absorbent article 5 has a greater fluid capacity than more peripherally located portions of the absorbent article 5. Further, a central colored region 60 that is darker than the outer colored region 100 may provide for improved stain masking in the portion of the absorbent article 5 with which the central colored region 60 is coordinated. It may not be desirable to mask a stain in the outer colored region 100 as much as in the central colored region 60 because if the wearer does not perceive the stain, she might not recognize that she should consider changing the absorbent article 5 in the near future. For the same reasons with respect ensuring that stains in relatively remote portions of the absorbent article 5 are apparent to the wearer, the central colored region 60 can be darker than the intermediate colored region 80 and the intermediate colored region 80 can be darker than the outer colored region 100.

Figure 3:
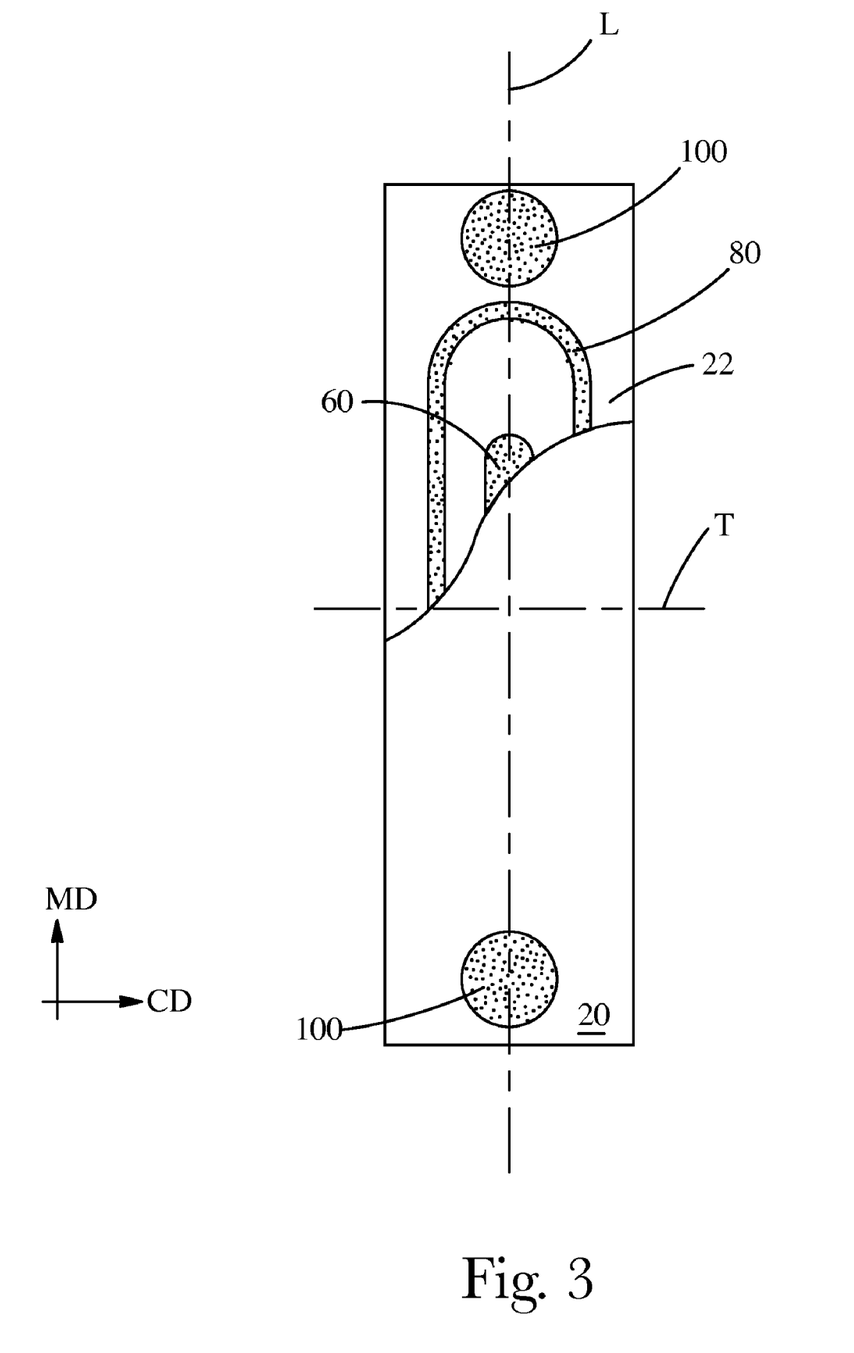
FIG. 3 is a schematic of an absorbent article.

As shown in FIG. 3, the absorbent article 5 can comprise a first layer 20 and a second layer 22. The first layer 20 can comprise a colored region selected from the group consisting of the central colored region 60, the intermediate colored region 80, and the outer colored region 100. The second layer 22 can comprise a colored region selected from the group consisting of the central colored region 60, the intermediate colored region 80, and the outer colored region 100, wherein the colored region of the first layer 20 differs from the colored region of the second layer 22. In such an embodiment, different colored regions can be located on different layers of the absorbent article 5, the layers being combined to create the overall visual impression. In manufacturing, the first layer 20 and second layer 22 can each be provided with the colored region or regions desired to be disposed thereon and the first layer 20 and second layer 22 can be combined in the manufacturing process It is thought that by having different colored regions on different layers of material of the absorbent article 5 that a richer visual impression can be created on the absorbent article 5. For instance, if the central colored region 60 and outer colored region 100 (or outer colored regions 100) are on different layers of materials, when viewed, at least one of the colored regions will viewed through the layer comprising the other colored region. A colored region viewed through another layer material can have a significantly different visual impression in terms of softness/diffuseness of the image, somewhat like the difference between a matte finished photograph versus a gloss finished photograph or the way an undergarment looks beneath a sheer article of clothing. Further, if the first layer 20 and second layer 22 are different material types, for example one is a film and the other is a nonwoven, different coloring techniques might be used on each layer. For instance, contact printing (e.g. gravure printing) might be employed for providing colored region on a film and inkjet printing might be employed to provide a colored region on a nonwoven. Such a multilayer approach might also allow changes in certain colored regions to be made conveniently on-line during manufacturing. For instance, a single manufacturing line could be used to produce a plurality of absorbent articles 5 having identical central colored regions 60 and outer colored regions 100 that vary from absorbent article 5 to absorbent article 5.

The first layer 20 can be a topsheet 30. The first layer 20 can be a fluid pervious polymer film or a nonwoven material. The first layer 20 can be a secondary topsheet 30 or insert, for instance an intermediate layer that is between the material in contact with the wearer's body when worn and the absorbent core 90 that is designed to collect and retain fluid. The first layer 20 can be an absorbent core 90. The first layer 20 can be a fibrous nonwoven wherein fibers from the nonwoven protrude through the second layer 22. Fibers from the nonwoven protruding through the second layer 22 can be provided by needle punching or other suitable method for moving the fibers of one web through another web such as disclosed in U.S. Pat. No. 7,410,683.

The second layer 22 can be a topsheet 30. The second layer 22 can be a fluid pervious polymer film, a nonwoven material, or another suitable fluid pervious material. The second layer 22 can be a secondary topsheet 30 or insert, for instance an intermediate layer that is between the material in contact with the wearer's body, such as the topsheet 30, when worn and the absorbent core 90 that is designed to collect and retain fluid. The second layer 22 can be an absorbent core 90.

Each of the central colored region 60, intermediate colored region 80, and outer colored region 100 can be provided to a layer by a technique selected from the group consisting of ink jet printing, gravure printing, flexographic printing, lithographic printing, and screen printing. In one embodiment of the method of fabricating, the coloration technique by which the central colored region 60 is colored differs from the coloration technique by which the outer colored region 100 is colored.

Figure 4:
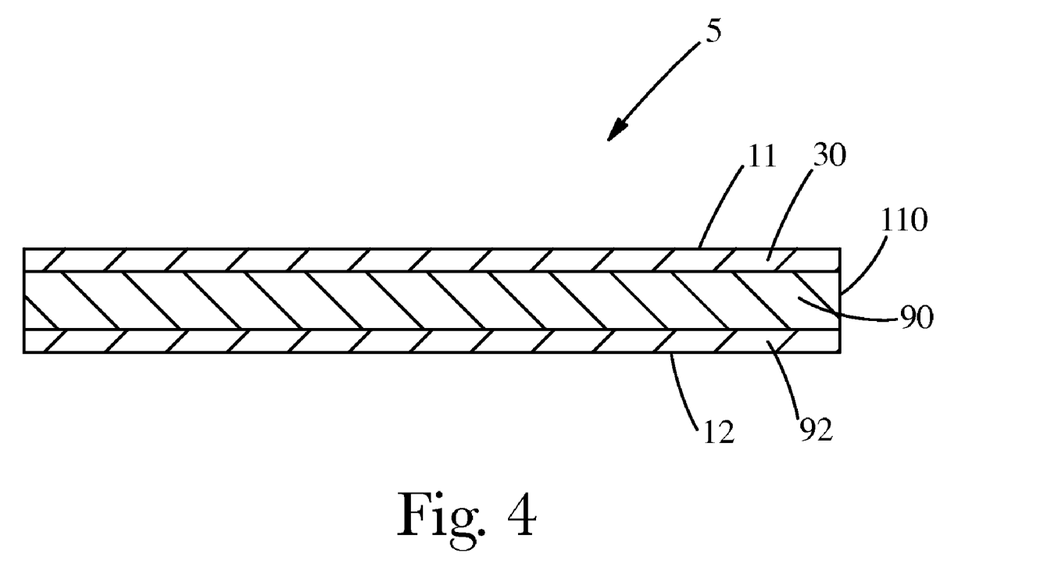
FIG. 4 is a cross-section of the absorbent article illustrated in FIG. 1.

A cross section of the absorbent article 5 illustrated in FIG. 1 is shown in FIG. 4. As illustrated, the absorbent article 5 can comprises a topsheet 30, a backsheet 92, and an absorbent core 90 disposed between the topsheet 30 and the backsheet 92. In some embodiments, each component of the absorbent article 5, and the absorbent article 5 itself, as illustrated in FIG. 4, can be considered to have a body facing side 11 and a garment facing side 12. The body facing side 11 being oriented towards the wearer's body or vaginal wall when the absorbent article is in-use and the garment facing side 12 opposing the body facing side 11. A tampon would not be considered to have a garment facing side since it is worn in the interior of the body.

Any of the central colored region 60, intermediate colored region 80, and outer colored region 100 can be disposed on or be part of any layer of the absorbent article 5 so long as these colored regions are visually perceptible from the body facing side 11 of the absorbent article 5. These colored regions can be located on, for example, the body facing side 11 or garment facing side 12 of any layer of the absorbent article 5. For instance, the central colored region 60 can be printed on the body facing side 11 of the absorbent core 90 and the outer colored region 100 can be printed on the garment facing side 12 of the topsheet 30. Any of the central colored region 60, intermediate colored region 80, and outer colored region 100 can be provided on an insert positioned between the topsheet 30 and the absorbent core 90.

Figure 5:
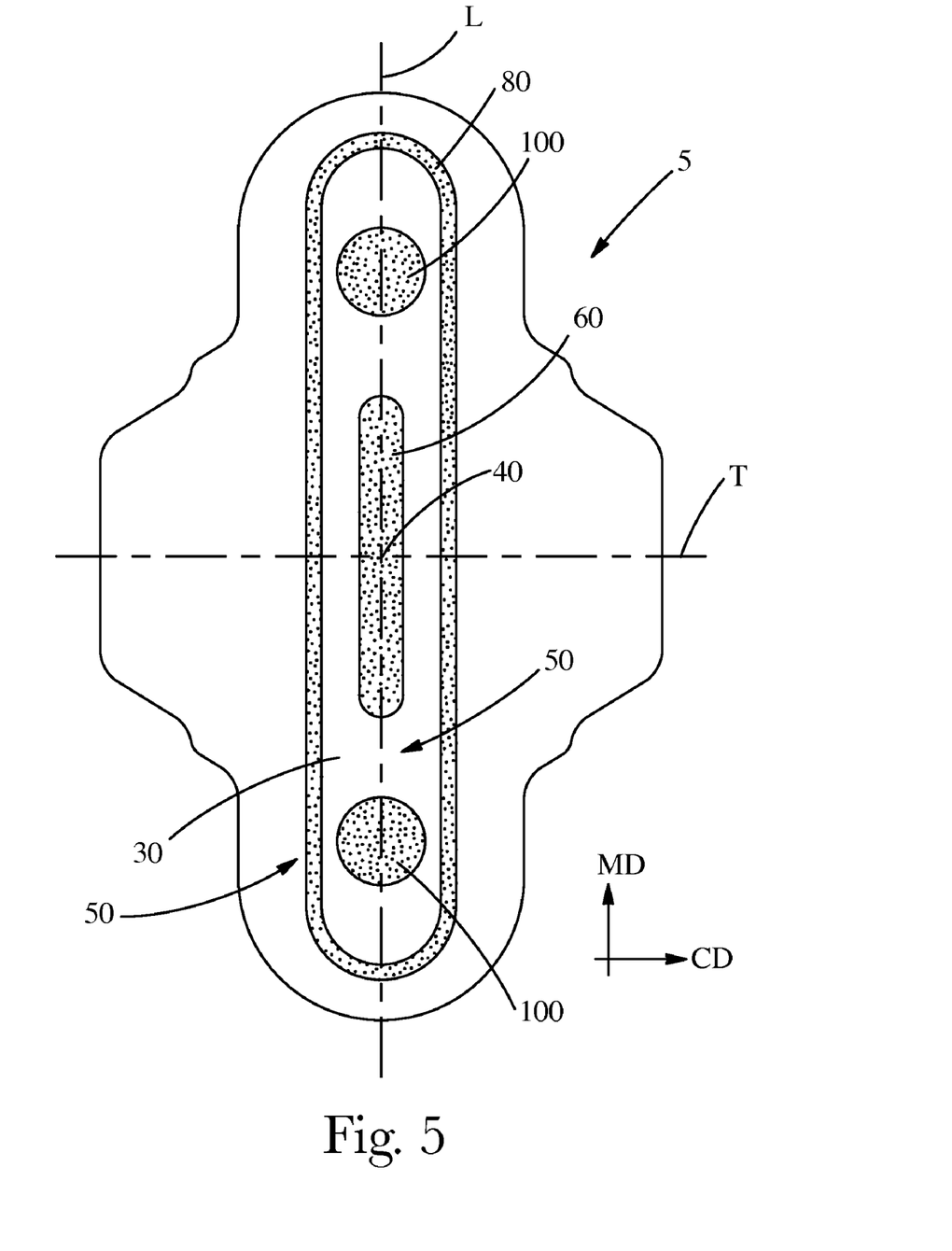
FIG. 5 is a schematic of an absorbent article.

As shown in FIG. 5, the outer colored region 100 can be positioned such that the outer colored region 100 is between the central colored region 60 and the intermediate colored region 80. Such an approach might be desirable if the intermediate colored region 80 is placed proximal the periphery 110, which might be perceived as a barrier to fluid flow.

The color of the central colored region 60, intermediate colored region 80, outer colored region 100, and background region 50 are measured by the reflectance spectrophotometer according to the colors L*, a*, and b* values. The L*, a*, and b* values are measured from the body facing surface 10 of the absorbent article 5 inboard of the periphery 110 of the absorbent article 5. The difference in color is calculated using the L*, a*, and b* values by the formula $\Delta E=[(L^*_X-L^*_Y)^2+(a^*_X-a^*_Y)^2+(b^*_X-b^*_Y)^2]^{1/2}$. Herein, the 'X' in the equation may represent the central colored region 60, the intermediate colored region 80, outer colored region 100, or the background region 50 and 'Y' may represent the color of another region against which the color of such region is compared. X and Y should not be the same two points of measurement at the same time. In other words, for any particular comparison of the difference in color, the location of X is not the same as the location of Y.

Where more than two colors are used, the 'X' and 'Y' values alternately include points of measurement in them also. The key to the $\Delta E$ calculation herein is that the 'X' and 'Y' values should not stem from the same measured point on the viewing surface. In those instances where there is effectively no background region 50 within the confines of the measurement area, the 'X' values should flow from a point different in spatial relationship to the 'Y' values, but within the confines of the periphery absorbent core 90.

Reflectance color is measured using the Hunter Lab LabScan XE reflectance spectrophotometer obtained from Hunter Associates Laboratory of Reston, Va. An absorbent article 5 is tested at an ambient temperature between 65° F. and 75° F. and a relative humidity between 50% and 80%.

The spectrophotometer is set to the CIELab color scale and with a D65 illumination. The Observer is set at 10° and the Mode is set at 45/0°. Area View is set to 0.125" and Port Size is set to 0.20". The spectrophotometer is calibrated prior to sample analysis utilizing the black glass and white reference tiles supplied from the vendor with the instrument. Calibration is done according to the manufacturer's instructions as set forth in LabScan XE User's Manual, Manual Version 1.1, August 2001, A60-1010-862. If cleaning is required of the reference tiles or samples, only tissues that do not contain embossing, lotion, or brighteners should be used (e.g., PUFFS tissue). Any sample point on the absorbent article containing the imparted color to be analyzed can be selected.

The absorbent article 5 is placed over the sample port of the spectrophotometer with a white clamp disk placed behind the absorbent article 5. The absorbent article 5 is to be in a substantially flat condition and free of wrinkles.

The absorbent article 5 is removed and repositioned so that a minimum of six readings of color of the body facing surface 10 are conducted. If possible (e.g., the size of the imparted color on the element in question does not limit the ability to have six discretely different, non-overlapping sample points), each of the readings is to be performed at a substantially different region on the externally visible surface so that no two sample points overlap. If the size of the colored region requires overlapping of sample points, only six samples should be taken with the sample points selected to minimize overlap between any two sample points. The readings are averaged to yield the reported L*, a*, and b* values for a specified color on an externally visible surface of an element.

In calculating the CIELab color space volume, V, maximum and minimum L*, a*, and b* values reported are determined for a particular set of regions to be measured. The maximum and minimum L*, a*, and b* values reported are used to calculate the CIELab color space volume, V, according to the following formula:

$$V = \frac{4}{3}\left|\frac{\Delta L^*}{2}\right|\left|\frac{\Delta a^*}{2}\right|\left|\frac{\Delta b^*}{2}\right|$$

Within the above formula, $\Delta L^*$ is the difference in L* values between the two colored regions being compared and is calculated by: $\Delta L^*=L^*_X-L^*_Y$. The $\Delta a^*$ is the difference in a* values between the two colored regions being compared and is calculated by: $\Delta a^*=a^*_X-a^*_Y$. The $\Delta b^*$ is the difference in b* values between the two colored regions being compared and is calculated by: $\Delta b^*=b^*_X-b^*_Y$. The CIELab color space volume can result in a solid substantially ellipsoidal in shape. If $\Delta L^*$, $\Delta a^*$, and $\Delta b^*$ are equal, the solid will be spherical. As used herein, a "solid" refers to the mathematical concept of a three-dimensional figure having length, breadth, and height (or depth). An ellipsoidal volume is preferred to calculate volume because an ellipsoid generally requires the dimensional differences of $\Delta L^*$, $\Delta a^*$, and $\Delta b^*$ to be relatively more uniform than other solids. Furthermore, it is believed that ellipsoidal volumes are more visually acceptable (i.e., less detectable color mismatch by human perception) than spherical volumes.

In some embodiments, the colors of at least two externally visible surfaces of discrete elements will occupy a CIELab color space volume of less than about 200. The externally visible surfaces are analyzed according to the Test Method described below. Upon analysis, the inherent color of an element comprising an externally visible surface will yield L*, a*, and b* coordinates. The CIELab color space volume is then calculated using the formula presented above. The resulting volume can be less than about 200. The resulting volume can be less than about 50.

It should be recognized that the colors of more than two discrete colored regions having a visible surface may occupy the aforementioned CIELab color space volumes. In calculating the CIELab color space volume for more than two elements, the CIELab color space volume is calculated using the maximum and minimum L*, a*, and b* from a set of elements. The maximum color values and minimum color values are used to calculate V according to the formula presented above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a centroid, a longitudinal centerline, a transverse centerline orthogonal to said longitudinal centerline and intersecting said longitudinal centerline at said centroid, and a body facing surface, said absorbent article comprising:
a background region;
a central colored region coincident with said longitudinal centerline;
an intermediate colored region substantially circumscribing said central colored region, wherein a portion of said intermediate colored region extends across said longitudinal centerline, wherein along said transverse centerline part of said background region is between said intermediate colored region and said central colored region; and
an outer colored region, wherein at least part of said background region is between said outer colored region and said intermediate colored region;
wherein said background region, said central colored region, said intermediate colored region, and said outer colored region are viewable from said body facing surface;
wherein said central colored region, said intermediate colored region, and said outer colored region differ in color from said background region.

2. An absorbent article according to claim 1, wherein said outer colored region is positioned such that said intermediate colored region is between said central colored region and said outer colored region.

3. An absorbent article according to claim 1, wherein said outer colored region is positioned such that said outer colored region is between said central colored region and said intermediate colored region.

4. An absorbent article according to claim 1, wherein said central colored region and said intermediate colored region are substantially spaced apart from one another.

5. An absorbent article according to claim 1, wherein said outer colored region is positioned on said longitudinal centerline.

6. An absorbent article according to claim 1, wherein said absorbent article comprises two outer colored regions, wherein said two outer colored regions are positioned on said longitudinal centerline, wherein said central colored region is between said two outer colored regions.

7. An absorbent article according to claim 1, wherein said absorbent article comprises two outer colored regions, wherein said two outer colored regions are spaced apart from one another such that said longitudinal centerline is between said two outer colored regions.

8. An absorbent article according to claim 1, wherein said absorbent article comprises two outer colored regions, wherein said two outer colored regions are spaced apart from one another such that said transverse centerline is between said two outer colored regions.

9. An absorbent article according to claim 1, wherein said absorbent article has a first end and a second end on opposing sides of said transverse centerline, wherein said first end comprises two outer colored regions each of which are on opposing sides of said longitudinal centerline, wherein said second end comprises two outer colored regions each of which are on opposing sides of said longitudinal centerline.

10. An absorbent article according to claim 1, wherein said absorbent article has a periphery, wherein said background region is between said central colored region and said periphery.

11. An absorbent article according to claim 1, wherein said absorbent article has a periphery, wherein said central colored region, said intermediate colored region, and said outer colored region are together substantially surrounded by said background region.

12. An absorbent article according to claim 1, wherein said central colored region, said intermediate colored region, and said outer colored region are within a CIELab color space volume of less than about 200.

13. An absorbent article according to claim 1, wherein said central colored region, said outer colored region, and said background region are measured by a Hunter Reflectance Meter test according to the colors $L^*$, $a^*$, and $b^*$, the $L^*$, $a^*$, and $b^*$ values being measured from said body facing surface, wherein said central colored region and said outer colored region have a color difference, the color difference being calculated using the $L^*$, $a^*$, and $b^*$ values by the formula $\Delta E=[(L^*_X-L^*_Y)^2+(a^*_X-a^*_Y)^2+(b^*_X-b^*_Y)^2]^{1/2}$, wherein said $\Delta E$ between said central colored region and said background region is at least about 1 and wherein said $\Delta E$ between said outer colored region and said background region is at least about 1.

14. An absorbent article according to claim 1, wherein said central colored region, said intermediate colored region, and said outer colored region are provided on a first layer of material in said absorbent article.

15. An absorbent article according to claim 1, wherein said absorbent article comprises a first layer and a second layer, wherein said first layer comprises a colored region selected from the group consisting of said central colored region, said intermediate colored region, and said outer colored region, wherein said second layer comprises a colored region selected from the group consisting of said central colored region, said intermediate colored region, and said outer colored region, wherein said colored region of said first layer differs from said colored region of said second layer.

16. An absorbent article according to claim 1, wherein said central colored region is darker than said outer colored region.

17. An absorbent article according to claim 15, wherein said first layer is a nonwoven and fibers from said nonwoven protrude through said second layer.

18. An absorbent article according to claim 1, wherein said intermediate colored region and said background region are measured by a Hunter Reflectance Meter test according to the colors $L^*$, $a^*$, and $b^*$, the $L^*$, $a^*$, and $b^*$ values being measured from said body facing surface, wherein said intermediate colored region has a color difference, the color difference being calculated using the $L^*$, $a^*$, and $b^*$ values by the formula $\Delta E=[(L^*_X-L^*_Y)^2+(a^*_X-a^*_Y)^2+(b^*_X-b^*_Y)^2]^{1/2}$, wherein said $\Delta E$ between said intermediate colored region and said background region is at least about 1.

19. An absorbent article according to claim 1, wherein said intermediate colored region radially circumscribes more than about 90% of said central colored region.

20. An absorbent article having a centroid, a longitudinal centerline, a transverse centerline orthogonal to said longitudinal centerline and intersecting said longitudinal centerline at said centroid, and a body facing surface, said absorbent article comprising:
a background region;
a central colored region coincident with said longitudinal centerline;

an intermediate colored region substantially circumscribing said central colored region, wherein a portion of said intermediate colored region extends across said longitudinal centerline, wherein along said transverse centerline part of said background region is between said intermediated colored region and said central colored region; and an outer colored region, wherein at least part of said background region is between said outer colored region and said intermediate colored region;

wherein said background region, said central colored region, said intermediate colored region, and said outer colored region are viewable from said body facing surface;

wherein said central colored region, said intermediate colored region, and said outer colored region differ in color from said background region;

wherein said first end comprises two outer colored regions each of which are on opposing sides of said longitudinal centerline;

wherein said second end comprises two outer colored regions each of which are on opposing sides of said longitudinal centerline;

wherein said intermediate colored region is between said central colored region and said outer colored regions;

wherein said outer colored regions are spaced apart from said intermediate colored region and said central colored region;

wherein said absorbent article comprises a first layer and a second layer, wherein said first layer comprises a colored region selected from the group consisting of said central colored region, said intermediate colored region, and said outer colored regions, wherein said second layer comprises a colored region selected from the group consisting of said central colored region, said intermediate colored region, and said outer colored regions, wherein said colored region of said first layer differs from said colored region of said second layer;

wherein said intermediate colored region radially circumscribes more than about 90% of said central colored region.

* * * * *